(12) United States Patent
Kume et al.

(10) Patent No.: US 10,918,634 B2
(45) Date of Patent: Feb. 16, 2021

(54) RESPIRATORY INFECTION TREATING AGENT

(71) Applicant: KYORIN PHARMACEUTICAL CO., LTD., Tokyo (JP)

(72) Inventors: Kota Kume, Tokyo (JP); Hisao Yoshida, Tokyo (JP); Hirotaka Ando, Tochigi (JP); Yuta Tanaka, Tochigi (JP)

(73) Assignee: KYORIN PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 16/189,461

(22) Filed: Nov. 13, 2018

(65) Prior Publication Data

US 2019/0076421 A1    Mar. 14, 2019

Related U.S. Application Data

(62) Division of application No. 15/554,329, filed as application No. PCT/JP2016/057797 on Mar. 11, 2016, now abandoned.

(30) Foreign Application Priority Data

Mar. 13, 2015  (JP) ................... 2015-051206
Jul. 8, 2015    (JP) ................... 2015-136944

(51) Int. Cl.
*A61K 31/4706* (2006.01)
*A61P 31/04* (2006.01)
*A61K 31/4709* (2006.01)

(52) U.S. Cl.
CPC .......... *A61K 31/4709* (2013.01); *Y02A 50/30* (2018.01)

(58) Field of Classification Search
CPC ................ C07D 401/04; C07D 498/06; A61K 31/4706; A61P 31/04; A61P 11/04
See application file for complete search history.

(56) References Cited

U.S. PATENT DOCUMENTS

| 6,194,434 B1 | 2/2001 | Takemura et al. | |
| 7,153,851 B2 * | 12/2006 | Asahina | C07D 498/06 514/230.2 |
| 7,514,451 B2 * | 4/2009 | Asahina | C07D 401/04 514/300 |
| 9,090,587 B2 * | 7/2015 | Araya | C07D 401/04 |
| 2005/0182052 A1 | 8/2005 | Asahina et al. | |
| 2006/0281779 A1 | 12/2006 | Asahina et al. | |
| 2010/0288310 A1 | 11/2010 | Krauss et al. | |

FOREIGN PATENT DOCUMENTS

| WO | 97/40037 | 10/1997 |
| WO | 03/078439 | 9/2003 |
| WO | 2005/026147 | 3/2005 |
| WO | 2013/069297 | 5/2013 |

OTHER PUBLICATIONS

International Search Report dated May 24, 2016 in International Application No. PCT/JP2016/057797.
Yoshikazu Asahina et al., "Synthesis and Antibacterial Activity of Novel Pyrido [1,2,3-de][1-4]benzoxazine-6-carboxylic Acid Derivatives Carrying the 3-Cyclopropylaminomethyl-4-substituted-1-pyrrolidinyl Group as a C-10 Substituent", Journal of Medicinal Chemistry, 2008, 51 (11), pp. 3238-3249.
Atsushi Fujita et al., "Levofloxacin Concentrations in Serum, Sputum, and Lung Tissue: Evaluation of its Efficacy According to Breakpoint", The Japanese Journal of Antibiotics, 1999, vol. 52, No. 11, pp. 661-666, with English translation.
Shigeo Yatagai et al, "Sputum-blood Concentration Ratio-time Profiles and Lung Tissues-blood Concentration Ratio of Sparfloxacin, a New Antibacterial Drug of the Fluoroquinolone Class", Clinical Report, Nov. 1996, vol. 30, No. 11, pp. 2997-3002, with English translation.
International Preliminary Report on Patentability dated Sep. 28, 2017 in International Application No. PCT/JP2016/057797.
Office Action dated Apr. 12, 2019 in Eurasian Patent Application No. 201791995.
"Pneumococcus", Wikipedia, dated Feb. 24, 2015; URL:https://ru.wikpedia.org/w/index.php?title=пНЕВМОКОКК&oldid=688334545> (the whole text), 4 pages.

* cited by examiner

*Primary Examiner* — D Margaret M Seaman
(74) *Attorney, Agent, or Firm* — Wenderoth, Lind & Ponack, L.L.P.

(57) ABSTRACT

[Problem] The present invention pertains to a safer and more effective respiratory infection treating agent.
[Solution] A respiratory infection treating agent containing, as an active ingredient, 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof.

9 Claims, 1 Drawing Sheet

RESPIRATORY INFECTION TREATING AGENT

TECHNICAL FIELD

The present invention relates to a respiratory infection treating agent.

BACKGROUND ART

Since the development of norfloxacin, quinolone carboxylic acid-based antibacterial agents called new quinolone have been developed worldwide. Currently, many new quinolone-based antibacterial agents are generally used as an infection treating agent.

On the other hand, a quinolone carboxylic acid derivative represented by a general formula (1) is disclosed by this applicant (Patent Literature 1).

[Chemical Formula 1]

In the formula (1), $R^1$ is an alkyl group having 1 to 6 carbon atoms of which 1 or 2 or more hydrogen atoms may be substituted with 1 or 2 or more halogen atoms, a cycloalkyl group which has 3 to 6 carbon atoms and may be substituted with 1 or 2 or more halogen atoms, or an aryl or heteroaryl group which may be substituted with 1 or 2 or more substituents which are the same or different and are selected from a halogen atom and an amino group; $R^2$ is a hydrogen atom, an alkyl group having 1 to 3 carbon atoms, or a pharmaceutically acceptable cation; $R^3$ is a hydrogen atom, a halogen atom, a hydroxyl group, an amino group, or an alkyl group having 1 to 3 carbon atoms; $R^4$ is a hydrogen atom or a halogen atom; $R^5$ is a fluorine atom; $R^6$ is a hydrogen atom or a fluorine atom; and A is a nitrogen atom or =C—X (wherein X is a hydrogen atom, a halogen atom, amino groups, cyano groups, or an alkyl or alkoxyl group which has 1 to 3 carbon atoms and may be substituted with 1 or 2 or more halogen atoms).

Patent Literature 1 also discloses 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid as one example of the quinolone carboxylic acid derivative. A hydrochloride salt thereof is disclosed in Patent Literature 2.

CITATION LIST

Patent Literature

Patent Literature 1: WO2005/026147
Patent Literature 2: WO2013/069297

SUMMARY OF INVENTION

Technical Problem

An object of the present invention is to provide a novel respiratory infection treating agent.

Solution to Problem

The present inventor has studied a safer and more effective respiratory infection treating agent.

As a result, the inventor has found that among quinolone carboxylic acid derivatives represented by the general formula (1), 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid and a pharmaceutically acceptable salt thereof, and in particular, a hydrochloride salt thereof have significantly high tissue distribution ratio into the respiratory organ (particularly, the lung) and distribute into the respiratory organ rapidly after administration, and therefore, are extremely useful as a respiratory infection treating agent. The present invention has thus been completed.

A summary of the present invention is as follows:

[1] A respiratory infection treating agent containing, as an active ingredient, 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof.

[2] The treating agent according to [1], wherein the respiratory infection treating agent is a respiratory infection treating agent for human.

[3] The treating agent according to [1] or [2], wherein the respiratory infection is one or two or more infections selected from the group consisting of pharyngitis, laryngitis, tonsillitis, acute bronchitis, pneumonia, and secondary infections of chronic respiratory diseases.

[4] The treating agent according to any one of [1] to [3], wherein pathogenic bacteria causing the respiratory infection are one or two or more types of bacteria selected from the group consisting of bacteria belonging to *Staphylococcus* sp., bacteria belonging to *Streptococcus* sp., *Moraxella catarrhalis*, bacteria belonging to *Klebsiella* sp., *Haemophilus influenzae*, and *Escherichia coli*.

[5] The treating agent according to any one of [1] to [4], wherein the pathogenic bacteria causing the respiratory infection are one or two or more types of bacteria belonging to any of *Streptococcus* sp. and *Staphylococcus* sp.

[6] The treating agent according to any one of [1] to [5], wherein the pathogenic bacteria causing the respiratory infection have drug resistance.

[7] The treating agent according to any one of [1] to [6], wherein the dose of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof per day is 10 mg or more and 250 mg or less.

[8] A treating agent for an infection which is one or two or more selected from the group consisting of pharyngitis, laryngitis, tonsillitis, acute bronchitis, pneumonia, secondary infections of chronic respiratory diseases, sinusitis, and tympanitis, and in which pathogenic bacteria are *Streptococcus pneumoniae*, the treating agent including, as an active ingredient, 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof.

[9] A method for treating a respiratory infection, including administering 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof in an amount effective to treat a respiratory infection to a subject in need thereof.

[10] The method according to [9], wherein the subject is human.

[11] The method according to [9] or [10], wherein the respiratory infection is one or two or more infections selected from the group consisting of pharyngitis, laryngitis, tonsillitis, acute bronchitis, pneumonia, and secondary infections of chronic respiratory diseases.

[12] The method according to any one of [9] to [11], wherein pathogenic bacteria causing the respiratory infection are one or two or more types of bacteria selected from the group consisting of bacteria belonging to *Staphylococcus* sp., bacteria belonging to *Streptococcus* sp., *Moraxella catarrhalis*, bacteria belonging to *Klebsiella* sp., *Haemophilus influenzae*, and *Escherichia coli*.

[13] The method according to any one of [9] to [12], wherein the pathogenic bacteria causing the respiratory infection are one or two or more types of bacteria belonging to any of *Streptococcus* sp. and *Staphylococcus* sp.

[14] The method according to any one of [9] to [13], wherein the pathogenic bacteria causing the respiratory infection have drug resistance.

[15] The method according to any one of [9] to [14], wherein the dose of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof per day is 10 mg or more and 250 mg or less.

[16] 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof for treating a respiratory infection.

[17] The compound for treatment of a respiratory infection according to [16], wherein the respiratory infection is a respiratory infection in human.

[18] The compound for treatment of a respiratory infection according to [16] or [17], wherein the respiratory infection is one or two or more infections selected from the group consisting of pharyngitis, laryngitis, tonsillitis, acute bronchitis, pneumonia, and secondary infections of chronic respiratory diseases.

[19] The compound for treatment of a respiratory infection according to any one of [16] to [18], wherein pathogenic bacteria causing the respiratory infection are one or two or more types of bacteria selected from the group consisting of bacteria belonging to *Staphylococcus* sp., bacteria belonging to *Streptococcus* sp., *Moraxella catarrhalis*, bacteria belonging to *Klebsiella* sp., *Haemophilus influenzae*, and *Escherichia coli*.

[20] The compound for treatment of a respiratory infection according to any one of [16] to [19], wherein the pathogenic bacteria causing the respiratory infection are one or two or more types of bacteria belonging to any of *Streptococcus* sp. and *Staphylococcus* sp.

[21] The compound for treatment of a respiratory infection according to any one of [16] to [20], wherein the pathogenic bacteria causing the respiratory infection have drug resistance.

[22] The compound for treating a respiratory infection according to any one of [16] to [21], wherein the dose of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof per day is 10 mg or more and 250 mg or less.

[23] Use of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof for manufacturing of a medicament for treatment of a respiratory infection.

[24] The use according to [23], wherein the respiratory infection is a respiratory infection in human.

[25] The use according to [22] or [24], wherein the respiratory infection is one or two or more infections selected from the group consisting of pharyngitis, laryngitis, tonsillitis, acute bronchitis, pneumonia, and secondary infections of chronic respiratory diseases.

[26] The use according to any one of [23] to [25], wherein pathogenic bacteria causing the respiratory infection are one or two or more types of bacteria selected from the group consisting of bacteria belonging to *Staphylococcus* sp., bacteria belonging to *Streptococcus* sp., *Moraxella catarrhalis*, bacteria belonging to *Klebsiella* sp., *Haemophilus influenzae*, and *Escherichia coli*.

[27] The use according to any one of [23] to [26], wherein the pathogenic bacteria causing the respiratory infection are one or two or more types of bacteria belonging to any of *Streptococcus* sp. and *Staphylococcus* sp.

[28] The use according to any one of [23] to [27], wherein the pathogenic bacteria causing the respiratory infection have drug resistance.

[29] The use according to any one of [23] to [28], wherein the dose of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof per day is 10 mg or more and 250 mg or less.

[30] A method for treating an infection which is one or two or more selected from the group consisting of pharyngitis, laryngitis, tonsillitis, acute bronchitis, pneumonia, secondary infections of chronic respiratory diseases, sinusitis, and tympanitis, and in which the pathogenic bacteria are *Streptococcus pneumoniae*, the method including administering 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof in an amount effective to treat the respiratory infection to a subject in need thereof.

[31] 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof for treatment of an infection which is one or two or more selected from the group consisting of pharyngitis, laryngitis, tonsillitis, acute bronchitis, pneumonia, secondary infections of chronic respiratory diseases, sinusitis, and tympanitis, and in which the pathogenic bacteria are *Streptococcus pneumoniae*.

[32] Use of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof in manufacturing of a medicament for treatment of an infection which is one or two or more selected from the group consisting of pharyngitis, laryngitis, tonsillitis, acute bronchitis, pneumonia, secondary infections of chronic respiratory diseases, sinusitis, and tympanitis, and in which the pathogenic bacteria are *Streptococcus pneumoniae*.

[33] The treating agent according to [8], wherein the dose of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof per day is 10 mg or more and 250 mg or less.

[34] The treating agent according to [1], wherein the dose of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof per day is 75 mg or two times the amount.

[35] A treating agent for an infection which is one or two or more selected from the group consisting of pharyngitis, laryngitis, tonsillitis, acute bronchitis, pneumonia, secondary infections of chronic respiratory diseases, sinusitis, and tympanitis, the treating agent containing 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof, wherein the dose of the compound per day is 75 mg or two times the amount.

[36] The treating agent according to [35], wherein pathogenic bacteria causing the infection are *Streptococcus pneumoniae*.

[37] The treating agent according to [1], wherein the maximum plasma concentration of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof after administration of the treating agent to human with a respiratory infection is 3 μg/mL or less.

[38] The treating agent according to [1], wherein the maximum plasma concentration of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof after administration of the treating agent to human with a respiratory infection is 0.5 μg/mL or more and 1.5 μg/mL or less.

[39] The treating agent according to [1], wherein the maximum plasma concentration of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof after administration of the treating agent to human with a respiratory infection is 0.7 μg/mL or more and 1.2 μg/mL or less.

[40] The treating agent according to [37], wherein the dose of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof per day is 75 mg or two times the amount.

[41] The treating agent according to [38] or (391, wherein the dose of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof per day is 75 mg.

[42] An infection treating agent containing 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof, wherein the tissue distribution ratio of the compound into an alveolar epithelial lining fluid 1 hour after administration to human is 10 or more.

[43] An infection treating agent containing 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof, wherein the tissue distribution ratio of the compound into an alveolar epithelial lining fluid 1 hour after administration to human is 10 or more and 50 or less.

[44] An infection treating agent containing 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof, wherein the tissue distribution ratio of the compound into an alveolar epithelial lining fluid 1 hour after administration to human is 15 or more and 40 or less.

Advantageous Effects of Invention

The present invention can provide a technique pertaining to a novel respiratory infection treating agent.

DESCRIPTION OF EMBODIMENTS

Hereinafter, one of embodiments of the present invention will be described in detail.

A treating agent of the embodiment relates to a respiratory infection treating agent, and for example, can be used for treatment of respiratory infection in human.

The respiratory infection means an infection caused at any location of the respiratory organ.

The respiratory organ collectively refers to the organ pertaining to respiration, and means the organ from the nasal vestibule to the alveolar through the nasal cavity, the pharynx, the larynx, the trachea, the bronchus, and the bronchiole.

Examples of the respiratory infection involved in the treating agent of the embodiment may include one or two or more respiratory infections selected from the group consisting of common cold, pharyngitis, laryngitis, epiglottitis, tonsillitis (including peritonsillitis and peritonsillar abscess), bronchitis (including acute bronchitis, chronic bronchitis, and diffuse panbronchiolitis), pneumonia, secondary infections of chronic respiratory diseases, and bronchiectasis.

In order to treat one or two or more respiratory infections selected from the group consisting of pharyngitis, laryngitis, tonsillitis, acute bronchitis, pneumonia, and secondary infections of chronic respiratory diseases among these infections, it is preferable that the treating agent of the embodiment be used. A target disease of the treating agent in a more preferred embodiment may be one or two or more types of respiratory infections selected from the group consisting of the acute bronchitis, pneumonia, and secondary infections of chronic respiratory diseases, since the compound according to the embodiment can be rapidly transferred to a location where symptom occurs to achieve more effective treatment.

Pathogenic bacteria causing the respiratory infection which is the target disease of the treating agent of the embodiment are, for example, one or two or more types of bacteria selected from the group consisting of bacteria belonging to *Staphylococcus* sp., bacteria belonging to *Streptococcus* sp., *Moraxella* (Branhamella) *catarrhalis*, bacteria belonging to *Klebsiella* sp., bacteria belonging to *Enterobacter* sp., *Haemophilus influenzae*, bacteria belonging to *Enterococcus* sp., *Escherichia coli*, *Pseudomonas aeruginosa*, *Legionella*, *Chlamydia*, *Mycoplasma*, *Coxiella burnetii*, *Bordetella pertussis*, and anaerobic bacteria.

The pathogenic bacteria for which the treating agent of the embodiment is used is more preferably one or two or more types of bacteria selected from the group consisting of bacteria belonging to *Staphylococcus* sp, bacteria belonging to *Streptococcus* sp., *Moraxella catarrhalis*, bacteria belonging to *Klebsiella* sp., bacteria belonging to *Enterobacter* sp., *Haemophilus influenzae*, *Legionella pneumophila*, *C. pneumoniae* (*Chlamydophila pneumoniae*), *M. pneumoniae* (*Mycoplasma pneumoniae*), and *Escherichia coli*, further preferably one or two or more types of bacteria selected from the group consisting of bacteria belonging to *Staphylococcus* sp., bacteria belonging to *Streptococcus* sp., *Moraxella catarrhalis*, bacteria belonging to *Klebsiella* sp., *Haemophilus influenzae*, and *Escherichia coli*, and particularly preferably one or two or more types of bacteria belonging to any of *Streptococcus* sp. and *Staphylococcus* sp.

Examples of pathogenic bacteria belonging to *Streptococcus* sp. may include Pneumococcus, *Streptococcus pyogenes*, hemolytic *streptococcus*, and *Streptococcus sanguinis*. Among these, the pathogenic bacteria for which the treating agent of the embodiment is used is preferably *Streptococcus pneumoniae*. Examples of the pathogenic bacteria belonging to *Staphylococcus* sp. may include *Staphylococcus aureus* and *Staphylococcus epidermidis*. Among these, the pathogenic bacteria for which the treating agent of the embodiment is used is preferably *Staphylococcus aureus*. Therefore, the treating agent of the embodiment can be used for treatment of one or two or more types of respiratory infections which are selected from the group consisting of acute bronchitis, pneumococcus, and secondary infections of chronic respiratory diseases and in which pathogenic bacteria are *Streptococcus pneumoniae* and/or *Staphylococcus aureus*.

Herein, pathogenic bacteria mean a concept including bacteria which have acquired drug resistance. The drug resistance means a phenomenon in which an organism has resistance to a drug and the drug is not effective or is unlikely to be effective. Examples of drug resistance may include resistance to penicillin, resistance to cephem, resistance to carbapenem, resistance to aminoglycoside, resistance to macrolide, resistance to lincomycin, resistance to trimethoprim-sulfa, resistance to tetracycline, resistance to metronidazole, resistance to glycopeptide, resistance to oxazolidinone, resistance to daptomycin, and resistance to quinolone.

Examples of the bacteria which have acquired drug resistance may include penicillin-resistant bacteria such as penicillin-resistant *Streptococcus pneumoniae* (PRSP), methicillin-resistant bacteria such as methicillin-resistant *Staphylococcus aureus* (MRSA) and methicillin-resistant *Staphylococcus epidemidis* (MRSE), vancomycin-resistant bacteria such as vancomycin-resistant *enterococcus* (VRE), macrolide-resistant bacteria such as macrolide-resistant *Streptococcus pneumoniae*, and quinolone-resistant bacteria such as quinolone-resistant *Streptococcus pneumoniae*.

A disease to be treated by the treating agent of the embodiment may be any of a respiratory infection in which the pathogenic bacteria are non-drug-resistant bacteria and a respiratory infection in which the pathogenic bacteria are bacteria which have acquired drug resistance, and is not particularly limited. On the other hand, since the treating agent of the embodiment also exhibits excellent therapeutic effect on a respiratory infection in which the pathogenic bacteria are bacteria which have acquired drug resistance, the pathogenic bacteria causing the target disease of the treating agent of the embodiment may be preferably quinolone-resistant bacteria, and more preferably quinolone-resistant *Streptococcus pneumoniae* and/or quinolone-resistant *Staphylococcus aureus*. Therefore, the treating agent of the embodiment can be used for treatment of one or two or more types of respiratory infections which are selected from the group consisting of acute bronchitis, pneumonia, and secondary infections of chronic respiratory diseases, and in which the pathogenic bacteria are quinolone-resistant *Streptococcus pneumoniae* and/or quinolone-resistant *Staphylococcus aureus*.

The treating agent of the embodiment may be composed of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof alone. The treating agent of the embodiment may be a pharmaceutical composition containing 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof, and another compound acting as an active ingredient, and/or a pharmaceutically acceptable additive.

The pharmaceutical composition can contain one or more types of compounds as the other compound acting as an active ingredient and/or as the pharmaceutically acceptable additive. The pharmaceutical composition can be prepared, for example, by mixing 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof with one or more types of the compound acting as an active ingredient or the additive.

Examples of the pharmaceutically acceptable additive contained with 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof may include an excipient, a lubricant, a binder, a disintegrant, a stabilizer, a flavoring agent, and a diluent. These additives are not particularly limited as long as they can be used for production of a pharmaceutical preparation, and for example, an additive listed in "Japanese Pharmaceutical Excipients Directory (International Pharmaceutical Excipients Council Japan, YAKUJI NIPPO, LTD. (2007)) can be appropriately used.

The treating agent of the embodiment can be administered to a subject such as human in a form well conventionally known as a pharmaceutical form through an administration route well conventionally known as a pharmaceutical route. For example, the treating agent may be orally or non-orally administered in a form of preparation such as a powder, a tablet, a capsule, a subtle granule, a granule, a syrup, an injection, an ophthalmic liquid, an aqueous nose drop, an aqueous ear drop, or an inhalant liquid. Specifically, the treating agent of the embodiment may be produced in the form exemplified above, for example, by mixing a physiologically acceptable carrier, excipient, binder, and diluent, and the like with the active ingredient.

In order to reduce a side effect, form a small preparation which can be easily administered, and prevent development of resistant bacteria, the dose of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof per day is preferably 10 mg or more and 250 mg or less, more preferably 20 mg or more and 200 mg or less, further preferably 30 mg or more and 160 mg or less, still more preferably 40 mg or more and 100 mg or less, yet more preferably 50 mg or more and 90 mg or less, and particularly preferably 60 mg or more and 80 mg or less. The treating agent in a daily dose may be administered once or in divided doses two to three times. It is preferable that the treating agent be administrated once per day. When the effect is insufficient, the treating agent may be used in an amount which is two times the daily dose.

In order to rapidly reach the target blood level, loading administration may be performed. The loading administration means an administration design in which the daily dose or the number of administration per day is increased at the early stage of administration to rapidly reach the target blood level. The early stage of administration means the first to third days of initiation of the administration, preferably the first to second days, and further preferably the first day of initiation of the administration. As an increased daily dose, an amount which is two times the daily dose is preferably used.

When the loading administration is performed, it is preferable that the amount which is two times the daily dose be used on the first day of initiation of administration.

A pharmaceutically acceptable salt of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid is not particularly limited as long as it is a pharmacologically acceptable salt. Examples thereof may include salts with inorganic acids such as hydrochloric acid, hydrobromic acid, sulfuric acid, and phosphoric acid, salts with organic acids such as maleic acid, fumaric acid, succinic acid, malic acid, malonic acid, methanesulfonic acid, toluenesulfonic acid, benzenesulfonic acid, lactic acid, oxalic acid, acetic acid, trifluoroacetic acid, and tartaric acid, and salts with metals such as sodium, potassium, magnesium, calcium, aluminum, cesium, chromium, cobalt, copper, iron, zinc, platinum, and silver. In particular, a hydrochloride salt is particularly preferable from the viewpoint of stability and the distribution ratio to the lung.

7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or the pharmaceutically acceptable salt thereof can be produced, for example, in accordance with the method described in Patent Literature 1 or 2.

Therefore, this embodiment can provide a technique pertaining to a novel treatment of a respiratory infection.

7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid and a pharmaceutically acceptable salt thereof, and in particular, a hydrochloride salt thereof have significantly high tissue distribution ratio into the respiratory organ (particularly, the lung) and distribute into the respiratory organ rapidly after administration. As compared with other quinolone compounds, the tissue distribution ratio into the respiratory organ in human is more excellent.

For example, the maximum plasma concentration of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof after administration of the treating agent according to the embodiment to human with a respiratory infection may be 3 μg/mL or less. In this case, the dose of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof per day may be 75 mg or two times the amount.

In a preferable aspect, the maximum plasma concentration of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof after administration of the treating agent according to the embodiment to human with a respiratory infection may be 0.5 μg/mL or more and 1.5 μg/mL or less, and in a more preferable aspect, the maximum plasma concentration may be 0.7 μg/mL or more and 1.2 μg/mL or less. In this case, the dose of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof per day may be 75 mg.

Therefore, the treating agent in a smaller dose than that of another drug can be expected to be effective against foci in the lung tissue or the like. Accordingly, a reduction in side effect, formation of a small preparation which can be easily administrated, prevention of development of resistant bacteria, and the like can be expected.

Further, the treating agent of the embodiment also exhibits excellent therapeutic effect on a respiratory infection in which the pathogenic bacteria are bacteria which have acquired drug resistance, such as quinolone-resistant bacteria.

Additionally, the treating agent of the embodiment has the property that the frequency of development of resistant bacteria is lower than those in the other quinolone compounds.

Therefore, this embodiment can provide a respiratory infection treating agent which has excellent effectiveness and safety.

EXAMPLES

Hereinafter, the present invention will be described more in detail with reference to Examples, but the present invention is not limited to the scope of the present invention by these Examples.

Reference Example 1-1

6,7-difluoro-1-(2-fluoroethyl)-8-methoxy-1,4-dihydro-4-oxo[2-$^{14}C_1$]quinoline-3-carboxylic Acid Ethyl Ester (Compound A-1)

[Chemical Formula 2]

(A-1)

A mixture (reaction liquid) of ethyl 3-(2,4,5-trifluoro-3-methoxy)phenyl-3-oxopropanate (1397.4 mg, 5.06 mmol), acetic anhydride (13.4 mL), and triethyl ortho[$^{14}C$]formate (293 mCi, 851 μL, 758 mg, 5.05 mmol, density: 0.891 g/mL) was heated and refluxed for 1 hour under a nitrogen atmosphere. The reaction liquid was cooled to room temperature, toluene (17 mL) was added to the reaction liquid, and the obtained mixture was concentrated under reduced pressure using a rotary evaporator. To the residue, toluene (17 mL) was added, and the mixture was concentrated under reduced pressure using a rotary evaporator. This operation was repeated 4 times, to obtain a yellow oily product.

To the residue as the obtained oily product, dimethylsulfoxide (13.4 mL), 2-fluoroethylamine hydrochloride (1259.84 mg, 12.7 mmol), and potassium carbonate (1745.4 mg, 12.6 mmol) were added to obtain a reaction liquid. The reaction liquid was stirred at 47° C. for 3 hours under a nitrogen atmosphere. To the reaction liquid, potassium carbonate (1752.9 mg, 12.7 mmol) was added, and the mixture was stirred at 78° C. for 1 hour, and then stirred at room temperature overnight, to obtain a reaction liquid. To the reaction liquid, water (50.5 mL) and acetone (8.4 mL) were added, and the mixture was stirred at room temperature for 20 minutes, and then stirred at 0° C. for 30 minutes, to obtain a precipitate. The precipitate was collected by filtration, and washed twice with a mixed liquid (5 mL) of water and acetone (water:acetone=6:1). The resulting solid was dried under reduced pressure to obtain 1286.8 mg of crude product.

To the obtained crude product, ethanol (24 mL) was added. The mixture was heated and refluxed under a nitrogen atmosphere until the solid was completely dissolved. The mixed solution was gradually cooled to room temperature, and water (5 mL) was added. After that, the mixture was stirred at room temperature for 20 minutes, and stirred at 10 to 15° C. for 30 minutes, to obtain a precipitate. The precipitate was collected by filtration, and washed twice with ethanol (1.6 mL). The solid was dried at 40° C. until the mass was constant.

To the obtained solid, ethanol (21.8 mL) was added, and the mixture was heated and refluxed under a nitrogen atmosphere until the solid was completely dissolved. The obtained solution was gradually cooled to room temperature, and stirred at 10 to 15° C. for 30 minutes, to obtain a precipitate. The precipitate was collected by filtration, washed twice with ethanol. (1.4 mL), and dried at 35 to 40° C. for 1 hour under reduced pressure. This operation was repeated twice or more to obtain 878.97 mg (2.65 mmol, 153.8 mCi, yield: 53%) of $^{14}$C-6,7-difluoro-1-(2-fluoroethyl)-8-methoxy-1,4-dihydro-4-oxo[2-$^{14}$C$_1$]quinoline-3-carboxylic acid ethyl ester (compound A-1).

Reference Example 1-2

6,7-difluoro-1-(2-fluoroethyl)-8-methoxy-1,4-dihydro-4-oxoquinoline-3-carboxylic Acid Ethyl Ester (Compound A-2)

[Chemical Formula 3]

(A-2)

Triethyl orthoformate was used instead of triethyl ortho[$^{14}$C]orthoformate, and the same operation as in Reference Example 1-1 was performed. Thus, 6,7-difluoro-1-(2-fluoroethyl)-8-methoxy-1,4-dihydro-4-oxoquinoline-3-carboxylic acid ethyl ester (compound A-2) was obtained.

Reference Example 2

Bis(acetato-O)-[6,7-difluoro-1-(2-fluoroethyl)-8-methoxy-4-oxo-1,4-dihydro[2-$^{14}$C$_1$]quinoline-3-carboxylato-O$^3$,O$^4$]boron (Compound B)

[Chemical Formula 4]

(B)

A mixed liquid (reaction liquid) of boric acid (954 mg, 15.4 mmol), acetic anhydride (8.4 mL), and zinc chloride (7.1 mg, 0.05 mmol) was stirred at room temperature for 10 minutes under a nitrogen atmosphere. To the reaction liquid, the compound A-1 (878 mg, 2.65 mmol) and the compound A-2 (400 mg, 1.22 mmol) were added. The reaction liquid was stirred at 55° C. for 2 hours under a nitrogen atmosphere. The reaction liquid was cooled to 30° C., and acetone (6.3 mL) was added to the reaction liquid. To a mixed solution of water (44.5 mL) and aqueous ammonia solution (28% w/w) (7.7 mL), the resulting mixed liquid containing acetone was added with stirring at 0° C. The mixed liquid was stirred at 0° C. for 30 minutes, to precipitate a white solid. The white solid was collected by filtration, and washed twice with water (1 mL). The resulting solid was dried at 65° C. under reduced pressure to obtain 1549.6 mg (143.2 mCi) of crude product.

To the obtained crude product, acetone (6.3 mL) was added. The mixture was heated and refluxed under a nitrogen atmosphere until the solid was completely dissolved. The mixed liquid was gradually cooled to room temperature, and isopropyl ether (6.3 mL) was added to the mixed liquid. After that, the mixture was stirred at room temperature for 15 minutes, and stirred at 10° C. for 30 minutes, to obtain a precipitate. The precipitate was collected by filtration, and washed twice with a mixed liquid (2 mL) of acetone and diisopropyl ether (1:2). The precipitate was dried at 65° C. under reduced pressure to obtain 1532.82 mg (3.56 mmol) of compound B (yield: 92%).

Reference Example 3

7-[(3S,4S)-3-{(cyclopropylamino)methyl}-4-fluoropyrrolidine-1-yl]-6-fluoro-1-(2-fluoroethyl)-8-methoxy-4-oxo-1,4-dihydro[2-$^{14}C_1$]quinoline-3-carboxylic Acid Hydrochloride (compound C)

[Chemical Formula 5]

(C)

A mixture (reaction liquid) of (3R,4S)-3-cyclopropylaminomethyl-4-fluoropyrrolidine (880 mg, 3.81 mol), triethylamine (2.9 mL, 2.1 g, 20.8 mmol), and dimethylsulfoxide (14.9 mL) was stirred at room temperature for 10 minutes under a nitrogen atmosphere. To the reaction liquid, the compound B prepared in Reference Example 2 (1489.2 mg, 3.46 mmol) was added, and the mixture was stirred at room temperature for 2 hours under a nitrogen atmosphere. To the reaction liquid, ethyl acetate (30 mL), water (30 mL), and an aqueous 2 mol/L sodium hydroxide solution (3.0 mL, 6.00 mmol) were added, and the mixture was stirred at room temperature for 5 minutes, and separated into an aqueous layer and an organic layer. The aqueous layer was washed twice with ethyl acetate (30 mL), and the combined organic layer was washed with water (30 mL) and saturated brine (30 mL), dried with anhydrous sodium sulfate, and concentrated under reduced pressure.

To the residue, 2-propanol (30 mL) and 2 mol/L hydrochloric acid (7.7 mL, 15.4 mmol) were added to obtain a reaction liquid. The reaction liquid was stirred at room temperature for 30 minutes. To the reaction liquid, 2-propanol (14.8 mL) was added, and the reaction liquid was stirred at 60° C. for 45 minutes. The reaction liquid was cooled to room temperature, and stirred at 0° C. for 30 minutes, to obtain a precipitate. The precipitate was collected by filtration, and washed three times with 2-propanol (1.5 mL). The resultant was dried under reduced pressure to obtain 843.53 mg of crude product.

To the obtained crude product, ethanol (30 mL) and water (2.6 mL) were added. The obtained solution was stirred at 97° C. for 25 minutes, and cooled to 25° C. at a speed of about 1° C./min. The solution was stirred at about 25° C. for 30 minutes, and stirred for 1 hour under ice-cooling, to obtain a precipitate. The precipitate was collected by filtration, washed twice with ethanol (3 mL), and dried at 50° C. A mother liquid was concentrated under reduced pressure, and dried at 50° C.

The product collected by filtration (569.2 mg, 47 mCi, 82.6 µCi/mg), the concentrated mother liquid (228.3 mg, 17.9 mCi, 78.4 µCi/mg), and a compound D (383.8 mg) were combined using ethanol (42 mL) and water (3.6 mL). The resulting mixture was stirred at 80° C. under a nitrogen atmosphere until the solid was completely dissolved. The mixed liquid was gradually cooled to 39 to 40° C. at a speed of 1° C./min. The mixed liquid was held to 39° C. for 30 minutes, and then gradually cooled to 23° C. at a speed of 1° C./min. The mixed liquid was held at room temperature for 30 minutes, and then held for 45 minutes under ice-cooling, to obtain a precipitate. The precipitate was collected by filtration, and washed twice with ethanol (3 mL), to obtain a white solid. The white solid was dried under reduced pressure, to obtain a compound C.

ESI MS (positive) m/z: 440 (M+H)$^+$, 442 (M+H)$^+$

Reference Example 4

7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic Acid Hydrochloride (Compound D)

7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid hydrochloride (compound D) was synthesized in accordance with the method of Example 1 in Patent Literature 2. The amounts of the compound D described in the following Test Examples were values in terms of free form.

[Test Example 1] Concentration in Tissue (Rat, Oral Administration)

The compound C (10.83 mg/kg) (solvent:water) was single orally administrated to a SD rat under fasting. 1, 6, and 24 hours after the administration, the lung tissue and the plasma were collected. The lung tissue was dried and treated by a sample oxidizer system (Sample Oxidizer: Model 307, PerkinElmer Inc., glass vial: 20 mL, Wheaton Industries, carbon dioxide absorbent: Carbo-Sorb 8 mL, PerkinElmer Inc., scintillation cocktail: Permafluor 12 mL, PerkinElmer Inc.), and the radioactivity concentration was measured. The plasma was fractionated in a midi-vial (8 mL, PerkinElmer Inc.), 6 mL of scintillation cocktail (Ultima Gold) was added, and the radioactivity concentration was measured. The radioactivity concentration was measured using a liquid scintillation counter (Tri-Carb 2500TR or 2700TR, PerkinElmer Inc.) (average value, n=3).

The results are shown in Table 1.

TABLE 1

| | RADIOACTIVITY CONCENTRATION IN TISSUE (µg eq./mL or g) | | | | | |
|---|---|---|---|---|---|---|
| | 1 hr | | 6 hr | | 24 hr | |
| | CONCENTRATION | TISSUE DISTRIBUTION RATIO* | CONCENTRATION | TISSUE DISTRIBUTION RATIO* | CONCENTRATION | TISSUE DISTRIBUTION RATIO* |
| PLASMA | 2.79 | — | 0.815 | — | 0.0294 | — |
| LUNG | 10.3 | 3.7 | 2.44 | 3.0 | 0.0541 | 1.9 |

*The tissue distribution ratio represents a value obtained by dividing the radioactivity concentration in the lung tissue by the radioactivity concentration in the plasma.

As seen from Table 1, the compound C distributed into the lung tissue rapidly after administration, and 1 hour after the administration, the tissue distribution ratio into the lung was as very high as "3.7".

This value was higher than values of marketed quinolone preparations, such as "2.7" of sitafloxacin (tissue distribution ratio into the lung tissue of a male rat 0.5 hours after single oral administration) (from the interview forms of Gracevit (registered trademark) tablets 50 mg and Gracevit (registered trademark) granules 10%), and "2.7" of ofloxacin (tissue distribution ratio into the lung tissue of a rat 1.0 hour after oral administration) (from the interview form of Tarivid (registered trademark) tablets 100 mg).

[Test Example 2] Concentration in Tissue (Human, Oral Administration)

Concentration of compound D in lung tissue (epithelial lining fluid and alveolar macrophages) and plasma was measured to investigate intrapulmonary distribution of compound D after oral single administration of this drug, with reference to a method in Document (Antimicrobial Agents and Chemotherapy, February 2010, pp. 866-870).

The measurement was as follows. Healthy adult male volunteers were given oral single dose of compound D (75 mg). The bronchioalveolar lavage fluid and blood samples were collected from the subjects at 1, 2, 4, 6, and 24 hours after the administration. The collection of the fluid and blood samples was carried out at each time point for six subjects. The bronchioalveolar lavage fluid was centrifuged to separate from epithelia lining fluid and alveolar macrophages for measurement of the drug concentration. The concentrations of compound D in lung tissue and plasma were measured by LC/MS/MS. The mean ratios of lung tissue-to-plasma concentration are shown as tissue distribution ratio in Table 2 at each sampling points.

TABLE 2

| | TISSUE DISTRIBUTION RATIO | | | | |
|---|---|---|---|---|---|
| | 1 hr | 2 hr | 4 hr | 6 hr | 24 hr |
| ALVEOLAR EPITHELIAL LINING FLUID | 22.5 | 18.4 | 16.5 | 15.2 | 15.0 |
| ALVEOLAR MACROPHAGES | 31.9 | 18.5 | 21.9 | 56.4 | 38.0 |

As shown in Table 2, the tissue distribution ratio of compound D in epithelial lining fluid and alveolar macrophages is extremely high with the ranges of 15.0-22.5 and 18.5-56.4, respectively. The compound D can reach to the respiratory infectious lesion with high concentration and indicate strong antibiotic action against the target pathogens causing respiratory tract infection. Therefore, it is suggested that compound D is particularly excellent for the treatment of respiratory tract infection.

Furthermore, the tissue distribution ratio of compound D at 1 hour after administration in epithelial lining fluid and alveolar macrophages is 22.5 and 31.9, respectively, which shows significantly good distribution. Initial antimicrobial effect after infection is important to the respiratory tract infection treatment. Compound D is distributed rapidly to intrapulmonary infectious lesion in one hour after administration. Therefore, compound D is especially useful for the treatment of respiratory tract infection.

The tissue distribution ratio in human of levofloxacin in the bronchioalveolar lavage fluid is 1.1 to 3.0 (0.5 to 8 hours after administration), and the tissue distribution ratio in the alveolar macrophages is 4.1 to 18.9 (0.5 to 24 hours after administration) (from the interview forms of Cravit (registered trademark) tablets 250 mg and 500 mg, and Cravit (registered trademark) granules 10%). The tissue distribution ratio in human of garenoxacin in the epithelial lining fluid is 0.95±0.41 (2.5 to 3.5 hours after administration), and the tissue distribution ratio in the alveolar macrophages is 11.15±8.16 (2.5 to 3.5 hours after administration) (from the interview form of Geninax (registered trademark) tablets 200 mg). The tissue distribution ratio in human of moxifloxacin in the airway secretory fluid is 6.78 (3 hours after administration), and the tissue distribution ratio in the alveolar macrophages is 18.59 (3 hours after administration) (from the interview form of Avelox (registered trademark) tablets 400 mg). These datas indicate that the tissue distribution ratio of compound D is remarkably high, compared with marketed quinolone.

It is excellent that the property of high distribution ratio of lung tissue can be expected high clinical efficacy with a small dosage. Due to this property, the daily dosage can be set to be lower compared with the other quinolone compounds. It is suggested that side effects can be reduced.

Due to the high distribution ratio into lung tissue, compound D can provide high concentration in the respiratory infectious lesion and can be contributed to preventing appearance of antimicrobial resistant bacteria.

These advantages contribute to the efficacy to respiratory tract infection of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof.

It is understood that an infection treating agent containing 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof and having a tissue distribution ratio of the compound into an alveolar epithelial lining fluid 1 hour after administration in administration to human of 10 or more can be configured. The tissue distribution ratio into alveolar epithelial lining fluid after 1 hour of administration is preferably within the range of 10 or more 50 or more less, and more preferably 15 or more 40 or more less.

[Test Example 3] Enzyme Inhibitory Activity of *Streptococcus pneumoniae*

The inhibitory activity of the compound D against DNA gyrase derived from *S. pneumoniae* IID553 was measured on the basis of the production amount of Supercoiled form DNA using Relaxed pBR322 as a substrate in accordance with Antimicrob. Agents Chemother. 47: 77-81 (2003). The inhibitory activity of the compound D against Topoisomerase IV was measured based on the production amount of Decatenated form DNA using Kinetoplast DNA as a substrate. Similarly, the inhibitory activities of levofloxacin (LVFX) and garenoxacin (GRNX) were measured. The results were compared. The results are shown in Table 3. The 50% inhibitory concentration ($IC_{50}$) value in Table 3 means an average value of results measured three times ±SD.

TABLE 3

| DRUG | IC$_{50}$ VALUE (μg/mL) | |
|---|---|---|
| | DNA gyrase | Topoisomerase IV |
| COMPOUND D | 6.0 ± 0.2 | 1.3 ± 0.3 |
| LVFX | 160 ± 40 | 11 ± 5 |
| GRNX | 36 ± 2 | 2.2 ± 0.5 |

In terms of inhibitory activity against an enzyme derived from *Streptococcus pneumoniae*, it can be seen that the compound D is more excellent than levofloxacin and garenoxacin.

[Test Example 4] Antibacterial Activity Against Quinolone-Resistant Strain (In Vitro)

The antibacterial activities in vitro of the compound D, levofloxacin, garenoxacin, and ciprofloxacin (CPFX) against quinolone-resistant strains of *Streptococcus pneumoniae* were measured in accordance with a Clinical and Laboratory Standards Institute (CLSI) microdilution method. The results are shown in Table 4.

TABLE 4

| No | STRAIN NAME | MUTATION | | MIC (μg/mL) | | | |
|---|---|---|---|---|---|---|---|
| | | gyrA | parC | COMPOUND D | LVFX | GRNX | CPFX |
| 1 | *S. pneumoniae* IID553 | NONE | NONE | 0.06 | 1 | 0.06 | 1 |
| 2 | *S. pneumoniae* NF9884 | NONE | Ser79Tyr | 0.125 | 2 | 0.125 | 2 |
| 3 | *S. pneumoniae* CF9842 | NONE | Asp81Phe | 0.06 | 2 | 0.125 | 2 |
| 4 | *S. pneumoniae* SF9863 | Ser81Phe | NONE | 0.06 | 2 | 0.25 | 2 |
| 5 | *S. pneumoniae* GF9821 | Ser81Tyr | NONE | 0.125 | 2 | 0.25 | 2 |
| 6 | *S. pneumoniae* ST9941 | Ser81Phe | Ser79Phe | 0.5 | 16 | 2 | 64 |
| 7 | *S. pneumoniae* SN9981 | Ser81Phe | Asp83Tyr | 0.25 | 16 | 1 | 32 |

In Table 4, the strain No. 1 is a non-quinolone-resistant strain (parent strain), and the strains No. 2 to 7 are a quinolone-resistant strain. As seen from the results, the compound D maintains excellent activity also against the quinolone-resistant strain as compared with the other quinolone compounds. In particular, the compound D exhibits high activity against the strains Nos. 6 (*S. pneumoniae* ST9941) and 7 (*S. pneumoniae* SN9981), which are a double mutant strain, as compared with the other quinolone compounds.

[Test Example 5] Antibacterial Activity Against *Streptococcus pneumoniae* (In Vitro)

The antibacterial activities in vitro of the compound D, garenoxacin, and levofloxacin against a strain in a mouse infected with *Streptococcus pneumoniae* (*S. pneumonia* KY-9) were measured in accordance with a CLSI microdilution method. The results are shown in Table 5.

TABLE 5

| STRAIN NAME | MIC (μg/mL) | | |
|---|---|---|---|
| | COMPOUND D | GRNX | LVFX |
| *S. pneumoniae* KY-9 | 0.06 | 0.03 | 1 |

[Test Example 6] Number of Bacteria in the Lung

*S. pneumoniae* KY-9 was inoculated at 7.4×10$^5$ CFU/mouse via the respiratory tract into the lung in a mouse in which cyclophosphamide had been administrated. 2.9 to 3.1 hours, 17.3 to 19.1 hours, and 24.4 to 26.1 hours after the inoculation, the drug (the compound D, levofloxacin, or garenoxacin) was subcutaneously administrated (SC) or orally administrated (PO) three times in total. The number of bacteria in the lung 16.5 to 17.0 hours after the final administration was measured. The results are shown in FIGS. 1 and 2.

Figure 1:
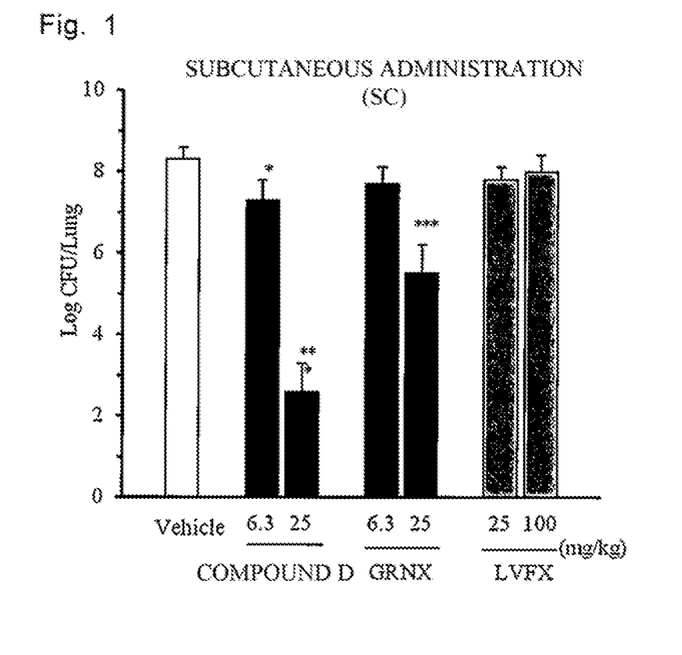
FIG. 1 is a graph showing the number of bacteria in the lung of mouse after subcutaneous administration of a drug in Test Example 6.
Figure 2:
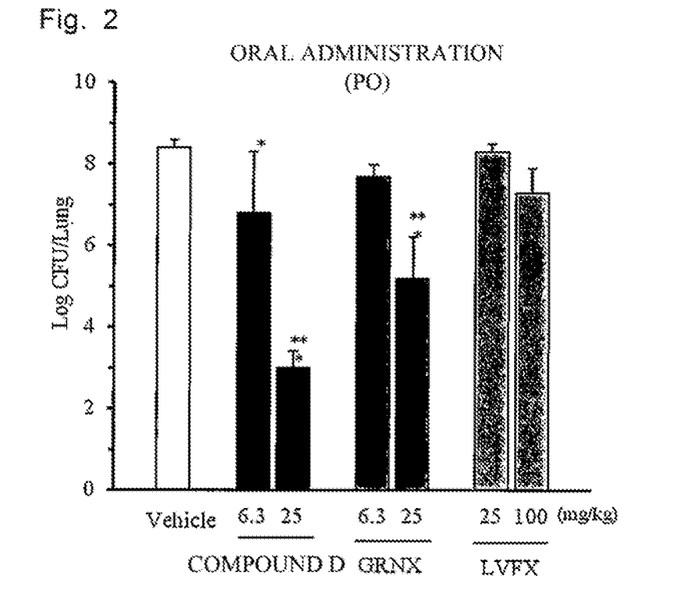
FIG. 2 is a graph showing the number of bacteria in the lung of mouse after oral administration of a drug in Test Example 6.

"*" described in FIGS. 1 and 2 means that a significant difference of $p<0.05$ in a Vehicle group was observed, and "**" means that a significant difference of $p<0.001$ in the Vehicle group was observed (Dunnett's multiple comparison test, parametric).

As seen from FIG. 1, after subcutaneous administration of the compound D (6.3 mg and 25 mg/kg), a significant dose-dependent decrease in number of bacteria in the lung was observed. After subcutaneous administration of garenoxacin of 6.3 mg/kg, a significant decrease in number of bacteria in the lung was not observed. However, when the dose of garenoxacin was increased to 25 mg/kg, a significant decrease in number of bacteria in the lung was observed. Here, CFU is an abbreviation of Colony Forming Unit, and represents the unit of number of bacteria. Log CFU/Lung means the number of viable bacteria in the lung. Log CFU/Lung was determined as follows. The lung obtained from the mouse was homogenated to obtain a bacterial culture. The bacterial culture was appropriately diluted, applied to an agar plate medium, and cultured. Log CFU/Lung was determined on the basis of the number of developed colonies.

The therapeutic effects of the compound D and garenoxacin in 25 mg/kg administration groups were compared. The number of viable bacteria in the lung for the compound D is $10^{2.6}$ CFU/Lung, and the number for garenoxacin is $10^{5.5}$ CFU/Lung. An about 1,000 times difference is observed. The minimum inhibitory concentration (MIC) of the compound D against *Streptococcus pneumoniae* (*S. pneumoniae* KY-9) is comparable with garenoxacin (see Table 5), but the compound D having excellent tissue distribution into the lung exerts a therapeutic effect which is higher than that of garenoxacin.

For levofloxacin, a significant decrease in number of bacteria in the lung was not found even after subcutaneous administration of 100 mg/kg.

FIG. 2 is a graph showing the number of bacteria in the lung after oral administration. Similarly to the subcutaneous administration, the therapeutic effect of the compound D is excellent as compared with garenoxacin and levofloxacin.

As seen from Test Examples 3 to 6, excellent effect of the compound D on *Streptococcus pneumoniae* can be understood and the compound D is effective as a treating agent for a disease in which the pathogenic bacteria are *Streptococcus* pneumoniae. Examples of the disease in which the pathogenic bacteria are *Streptococcus pneumoniae* may include otolaryngologic diseases such as sinusitis and tympanitis, in addition to respiratory infections such as pharyngitis, laryngitis, tonsillitis, acute bronchitis, pneumonia, and secondary infections of chronic respiratory diseases.

Therefore, as one aspect of the present invention, a treating agent for an infection which is one or two or more selected from the group consisting of pharyngitis, laryngitis, tonsillitis, acute bronchitis, pneumonia, secondary infections of respiratory diseases, sinusitis, and tympanitis and in which the pathogenic bacteria are *Streptococcus pneumoniae*, the treating agent containing, as an active ingredient, 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof can be exemplified.

[Test Example 7] Antibacterial Activity Against Clinically Isolated Strain (In Vitro)

The antibacterial activities in vitro of the compound D, garenoxacin, and levofloxacin against each clinically isolated strain of *Streptococcus pneumoniae, Moraxella catarrhalis*, and *Haemophilus influenzae* were measured in accordance with a CLSI microdilution method or a CLSI agar dilution method. A $MIC_{90}$ value was the minimum concentration in which the growth of 90% strain of all the measured strains was inhibited. The results are shown in Table 6.

TABLE 6

| STRAIN NAME AND | $MIC_{90}$ (μg/mL) | | |
|---|---|---|---|
| STRAIN NUMBER | COMPOUND D | GRNX | LVFX |
| PSSP[1] (26 STRAINS) | 0.06 | 0.06 | 1 |
| PCG-LOW SENSITIVE *S. pneumoniae* (22 STRAINS) | 0.06 | 0.06 | 1 |
| *M. catarrhalis*[2] (26 STRAINS) | 0.06 | 0.015 | 0.03 |
| *H. influenzaes*[3] (26 STRAINS) | 0.06 | 0.015 | 0.03 |

[1]PSSP means Penicillin-Resistant *Stereptococcus Pneunomiae*.
[2]AMPICILLIN-INSENSITIVE STRAIN; 7 STRAINS, AMPICILLIN-SENSITIVE STRAIN; 19 STRAINS
[3]AMPICILLIN-INSENSITIVE STRAIN; 2 STRAINS, AMPICILLIN-SENSITIVE STRAIN; 24 STRAINS

[Test Example 8] AUC and Cmax

Six Japanese healthy adult males received oral doses of 75 mg compound D once daily for seven consecutive days. The plasma concentration of compound D was measured by the HPLC method, and the pharmacokinetic parameters were calculated.

The maximum drug concentration (Cmax) value and the area under the curve (AUC) on day 7 was 0.998 μg/mL and 20.6 μg·h/mL, respectively. These values were very low as compared with garenoxacin or levofloxacin. After consecutive administration of garenoxacin in a daily dose of 400 mg, Cmax is 11.06 μg/mL and AUC is 110.9 μg·h/mL (Japanese Journal of Chemotherapy Vol. 55, No. S-1, pp. 95 to 115). After consecutive administration of levofloxacin in a daily dose of 500 mg, Cmax is 6.32 μg/mL and AUC is 49.67 μg·h/mL (Japanese Journal of Chemotherapy Vol. 57, No. 5-2, pp. 1 to 10).

[Test Example 9] Clinical Efficacy

We investigated efficacy of compound D for the patients with community-acquired pneumonia. 50 patients with community-acquired pneumonia were orally administered 75 mg of compound D once daily for 7 days. The clinical efficacy (cure rate) was evaluated at seven days after treatment completion. The clinical trial was performed in accordance with a part of evaluation on patients with community-acquired pneumonia (pp. 34 to 38) in "general guidelines for the evaluation of new antimicrobial agents for the treatment of respiratory tract infections (second version)."

The clinical efficacy (cure rate) of the compound D was 90.0%. This efficacy rate is not less than those of garenoxacin and levofloxacin.

In the clinical trial of 400 mg of garenoxacin for the patient with bacterial pneumonia, the clinical efficacy rate was 94.9% (Japanese Journal of Chemotherapy Vol. 55, No. S-1, pp. 127 to 142). In the clinical trial of 500 mg of levofloxacin for patients with community-acquired pneumonia, bacterial respiratory infection secondary to chronic respiratory diseases and acute bronchitis, the clinical efficacy rate was 89.3% (Japanese Journal of Chemotherapy Vol. 57, No. S-2, pp. 20 to 32).

From the results of Test Examples 7 to 9, the MIC of compound D is not less than those of garenoxacin and levofloxacin (Test Example 7). Although the concentration of compound D in plasma is low (see Test Example 8), the compound D indicate the therapeutic high efficacy rate similar to garenoxacin and levofloxacin for the treatment of respiratory tract infection (Test Example 9)

As shown in Table 2, compound D has very excellent distribution into lung tissue in human. Therefore, compound D can indicate high therapeutic efficacy even with low plasma concentration. Compound D does not need high plasma concentration unlike another drug. For this reason, the dose of compound D can be reduced, and it can be expected to reduce side effects and miniaturize the formulation which can be easily administrated.

[Test Example 10] Frequency of Development of Resistant Bacteria

The frequencies of development of bacteria resistant to the compound D, levofloxacin, garenoxacin, and ciprofloxacin for *S. aureus* ATCC29213, *S. pneumoniae* ATCC49619, and *E coli* ATCC25922 were investigated. During cultivation of strains for about 70 hours in the presence of a drug having a concentration 4, 8, and 16 times (4×MIC, 8×MIC, and 16×MIC) the MIC value of each strain, the frequency of development of resistant bacteria was investigated.

*S. aureus* ATCC29213 is *Staphylococcus aureus, S. pneumoniae* ATCC49619 is *Streptococcus pneumoniae*, and *E. coli* ATCC25922 is *Escherichia coli*. *Escherichia coli* is known as a main causative microorganism of chronic respiratory tract infection.

The frequency of development of resistant bacteria was calculated by dividing the number of colonies developed on an agar medium having each drug concentration by the number of initially inoculated bacteria.

The results are shown in Table 7.

TABLE 7

| STRAIN | DRUG | MIC (μg/mL) | FREQUENCY OF DEVELOPMENT OF RESISTANT BACTERIA (AVERAGE OF TWO MEASURED VALUES) | | |
|---|---|---|---|---|---|
| | | | 4 × MIC | 8 × MIC | 16 × MIC |
| S. aureus ATCC29213 | COMPOUND D | 0.008 | $<2.1 \times 10^{-9}$ | $<2.1 \times 10^{-9}$ | $<2.1 \times 10^{-9}$ |
| | LVFX | 0.125 | $<2.1 \times 10^{-9}$ | $<2.1 \times 10^{-9}$ | $<2.1 \times 10^{-9}$ |
| | GRNX | 0.015 | $8.2 \times 10^{-9}$* | $<2.1 \times 10^{-9}$ | $<2.1 \times 10^{-9}$ |
| | CPFX | 0.25 | $6.2 \times 10^{-9}$* | $3.1 \times 10^{-9}$* | $<2.1 \times 10^{-9}$ |
| E. coli ATCC25922 | COMPOUND D | 0.06 | $<1.9 \times 10^{-9}$ | $<1.9 \times 10^{-9}$ | $<1.9 \times 10^{-9}$ |
| | LVFX | 0.015 | $3.9 \times 10^{-9}$* | $<1.9 \times 10^{-9}$ | $<1.9 \times 10^{-9}$ |
| | GRNX | 0.03 | $<1.9 \times 10^{-9}$ | $<1.9 \times 10^{-9}$ | $<1.9 \times 10^{-9}$ |
| | CPFX | 0.008 | $1.2 \times 10^{-8}$* | $<1.9 \times 10^{-9}$ | $<1.9 \times 10^{-9}$ |
| S. pneumoniae ATCC49619 | COMPOUND D | 0.06 | $<1.1 \times 10^{-8}$ | $<1.1 \times 10^{-8}$ | $<1.1 \times 10^{-8}$ |
| | LVFX | 1 | $<1.1 \times 10^{-8}$ | $<1.1 \times 10^{-8}$ | $<1.1 \times 10^{-8}$ |
| | GRNX | 0.06 | $<1.1 \times 10^{-8}$ | $<1.1 \times 10^{-8}$ | $<1.1 \times 10^{-8}$ |
| | CPFX | 1 | $1.1 \times 10^{-8}$* | $<1.1 \times 10^{-8}$ | $<1.1 \times 10^{-8}$ |

CULTIVATION TIME: The cultivation time for S. aureus and E. coli was 70 hours 50 minutes, and the cultivation time for S. pneumoniae was 69 hours.

In Table 7, * shows that resistant bacteria were developed.

The development of bacteria resistant to the compound D for all the three types of bacteria which had been evaluated was not observed.

On the other hand, bacteria resistant to levofloxacin were developed for E. coli ATCC25922, and bacteria resistant to garenoxacin were developed for S. aureus ATCC29213. For all the three types of bacteria, bacteria resistant to ciproxacin were developed.

The results suggest that the bacteria resistant to the compound D are unlikely to be developed as compared with the other quinolone compounds.

[Test Example 11] Enzyme Inhibitory Activity of Staphylococcus aureus

The inhibitory activities of the compound D against DNA gyrase derived from S. aureus and quinolone-resistant S. aureus were measured on the basis of the production amount of Supercoiled form DNA using Relaxed pBR322 as a substrate in accordance with Antimicrob. Agents Chemother. 45: 3544-3547 (2001). The inhibitory activity of the compound D against Topoisomerase IV was measured on the basis of the production amount of Decatenated form DNA using Kinetoplast DNA as a substrate. The measurement was performed in the same manner as in Test Example 3. Similarly, the inhibitory activities of ciproxacin, levofloxacin, and garenoxacin were measured. The results were compared.

The results are shown in Tables 8 to 9.

TABLE 8

| | $IC_{50}$ VALUE (μg/mL) | |
|---|---|---|
| DRUG | DNA gyrase | QUINOLONE RESISTANT DNA gyrase |
| COMPOUND D | 1.7 ± 0.4 | 17 ± 3 |
| CPFX | 25 ± 5 | >1200 |

TABLE 8-continued

| | $IC_{50}$ VALUE (μg/mL) | |
|---|---|---|
| DRUG | DNA gyrase | QUINOLONE RESISTANT DNA gyrase |
| LVFX | 16 ± 6 | 1300 ± 100 |
| GRNX | 11 ± 1 | 420 ± 80 |

$IC_{50}$ VALUE: AVERAGE OF THREE MEASURED VALUES OR AVERAGE ± SD

TABLE 9

| | $IC_{50}$ VALUE (μg/mL) | |
|---|---|---|
| DRUG | Topoisomerase IV | QUINOLONE RESISTANT Topoisomerase IV |
| COMPOUND D | 0.73 ± 0.06 | 2.8 ± 0.3 |
| CPFX | 1.6 ± 0.7 | 69 ± 7 |
| LVFX | 2.8 ± 0.9 | 86 ± 19 |
| GRNX | 1.9 ± 0.6 | 27 ± 1 |

$IC_{50}$ VALUE: AVERAGE OF THREE MEASURED VALUES ± SD

As understood from Tables 8 and 9, the inhibitory effects of the compound D against DNA gyrase derived from S. aureus and Topoisomerase TV are higher than those of the other compounds regardless of whether or not each enzyme is derived from a quinolone-resistance strain.

The comparison of the inhibitory effect against an enzyme derived from a non-quinolone-resistant strain and the inhibitory effect against an enzyme derived from a quinolone-resistant strain suggests that the inhibitory activities of the compound D against these enzymes are unlikely to be affected by quinolone-resistant mutation as compared with the other compounds.

[Test Example 12] Antibacterial Activity Against Quinolone-Resistant Strain (In Vitro)

The antibacterial activities in vitro of the compound D, levofloxacin, garenoxacin, and ciprofloxacin against a quinolone-resistant strain of Streptococcus pneumoniae were measured in accordance with a CLSI agar microdilution method or a CLSI microdilution method.

The results are shown in Table 10.

TABLE 10

| STRAIN NAME | MUTATION LEVEL OF QUINOLONE RESISTANCE | MUTATION gyrA | MUTATION grlA | MIC (µg/mL) COMPOUND D | LVFX | GRNX | CPFX |
|---|---|---|---|---|---|---|---|
| S. aureus MS5935 | PARENT STRAIN | None | None | 0.015 | 0.125 | 0.015 | 0.25 |
| S. aureus MS5935 gyrA mutant | gyrA MUTANT STRAIN | Ser84Leu | None | 0.03 | 0.25 | 0.06 | 0.25 |
| S. aureus MS5935 1st | 1st step grlA MUTANT STRAIN | None | Ser80Phe | 0.03 | 0.5 | 0.03 | 2 |
| S. aureus MS5935 2nd | 2nd step grlA, gyrA DOUBLE MUTANT STRAIN | Ser84Leu | Ser80Phe | 0.125 | 8 | 2 | 16 |
| S. aureus MS5935 3rd | 3rd step grlA, gyra, grlA TRIPLE MUTANT STRAIN | Ser84Leu | Ser80Phe, Glu84Lys | 0.5 | 32 | 8 | 32 |
| S. aureus MS5935 4th | 4th step grlA, gyrA, grlA, gyrA QUADRUPLE MUTANT STRAIN | Ser84Leu, Glu88Val | Ser80Phe, Glu84Lys | 2 | 128 | 32 | 32 |

As seen from Table 10, the compound D maintains excellent activity also against the quinolone-resistant strain in addition to a parent strain (non-quinolone-resistant strain) as compared with the other quinolone compounds. The MIC of the compound D against high quinolone-resistant *S. aureus* (4th step grlA, gyrA, grlA, gyrA quadruple mutant strains) was 2 µg/mL, and the potency (action strength) 16 or more times those of the other quinolone compounds was observed.

INDUSTRIAL APPLICABILITY

The embodiment can provide a novel respiratory infection treating agent containing 7-[(3S,4S)-3-{(cyclopropylamino)methyl}-4-fluoropyrrolidine-1-yl]6-fluoro-1-(2-fluoroethyl)-8-methoxy-4-oxo-1,4-dihydroquinoline-3-carboxylic acid or a pharmaceutically acceptable salt thereof, which is industrially useful.

The invention claimed is:

1. A method of treating a respiratory infection comprising, administering a compound, wherein the compound is 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof, in an amount effective to treat the respiratory infection to a subject in need thereof,
wherein the subject is human and
wherein a dose of the compound per day is 75 mg or 150 mg.

2. The method of claim 1, wherein the respiratory infection is one or more infections selected from the group consisting of pharyngitis, laryngitis, tonsillitis, acute bronchitis, pneumonia, and secondary infections of chronic respiratory diseases.

3. The method of claim 1, wherein pathogenic bacteria causing the respiratory infection are one or more types of bacteria selected from the group consisting of bacteria belonging to *Staphylococcus* sp., bacteria belonging to *Streptococcus* sp., *Moraxella catarrhalis*, bacteria belonging to *Klebsiella* sp., *Haemophilus influenzae*, and *Escherichia coli*.

4. The method of claim 3, wherein the pathogenic bacteria causing the respiratory infection are bacteria belonging to *Streptococcus* sp. or *Staphylococcus* sp.

5. The method of claim 3, wherein pathogenic bacteria causing the respiratory infection have drug resistance.

6. A method of treating an infection which is one or more infections selected from the group consisting of pharyngitis, laryngitis, tonsillitis, acute bronchitis, pneumonia, secondary infections of chronic respiratory diseases, sinusitis, and tympanitis, and in which pathogenic bacteria are *Streptococcus pneumoniae*, the method comprising, administering a compound, wherein the compound is 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof, in an amount effective to treat the respiratory infection to a subject in need thereof,
wherein the subject is human and
wherein a dose of the compound per day is 75 mg or 150 mg.

7. A method of treating an infection which is one or more infections selected from the group consisting of pharyngitis, laryngitis, tonsillitis, acute bronchitis, pneumonia, secondary infections of chronic respiratory diseases, sinusitis, and tympanitis, the method comprising administering a compound, wherein the compound is 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof, to a subject in need thereof wherein a dose of the compound per day is 75 mg or 150 mg,
wherein the subject is human.

8. The method of claim 1, wherein a maximum plasma concentration of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof after administration to the subject is 3 µg/mL or less.

9. The method of claim 1, wherein a tissue distribution ratio of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a pharmaceutically acceptable salt thereof into an alveolar epithelial lining fluid 1 hour after administration to the subject is 10 or more.

* * * * *